United States Patent
Horrell et al.

(10) Patent No.: US 10,437,844 B2
(45) Date of Patent: Oct. 8, 2019

(54) DYNAMIC REGROUPING AND PRESENTATION OF ELECTRONIC PATIENT RECORDS

(71) Applicants: Robin Horrell, Billings, MT (US); Ronald H. Gorden-Ross, Lawrence, KS (US)

(72) Inventors: Robin Horrell, Billings, MT (US); Ronald H. Gorden-Ross, Lawrence, KS (US)

(73) Assignee: BILLINGS CLINIC, Billings, MT (US)

(*) Notice: Subject to any disclaimer, the term of this patent is extended or adjusted under 35 U.S.C. 154(b) by 625 days.

(21) Appl. No.: 14/324,616

(22) Filed: Jul. 7, 2014

(65) Prior Publication Data

US 2015/0019261 A1   Jan. 15, 2015

Related U.S. Application Data

(60) Provisional application No. 61/844,412, filed on Jul. 9, 2013, provisional application No. 61/985,324, filed on Apr. 28, 2014.

(51) Int. Cl.
*G06F 19/00* (2018.01)
*G06F 16/248* (2019.01)
*G16H 10/60* (2018.01)

(52) U.S. Cl.
CPC ........... *G06F 16/248* (2019.01); *G16H 10/60* (2018.01)

(58) Field of Classification Search
None
See application file for complete search history.

(56) References Cited

U.S. PATENT DOCUMENTS

| | | | | |
|---|---|---|---|---|
| 5,924,074 A | * | 7/1999 | Evans | G06F 19/325 705/3 |
| 2003/0220817 A1 | * | 11/2003 | Larsen | G06Q 50/22 705/2 |
| 2005/0197859 A1 | * | 9/2005 | Wilson | G16H 10/65 705/2 |
| 2006/0036471 A1 | * | 2/2006 | Sanjay-Gopal | G06Q 50/22 705/3 |

* cited by examiner

*Primary Examiner* — Michael Tomaszewski
(74) *Attorney, Agent, or Firm* — Tysver Beck Evans, PLLC

(57) ABSTRACT

A computerized system manages health documents in a computer database. Each document in the database is associated with an author, which is in turn associated with group. When documents for a patient are listed for a user, the computerized system uses the user's own group assignment within the database to organize and present the patient documents. Rules associated with the user's group create ad hoc categories of documents that are of special interest to the user.

14 Claims, 12 Drawing Sheets

DYNAMIC REGROUPING AND PRESENTATION OF ELECTRONIC PATIENT RECORDS

RELATED APPLICATIONS

The present application claims the benefit of U.S. Provisional Patent Application No. 61/844,412, filed on Jul. 9, 2013, and U.S. Provisional Patent Application No. 61/985,324, filed on Apr. 28, 2014, which are both hereby incorporated by reference in their entireties.

FIELD OF THE INVENTION

The present application relates to the field of electronic patient records. More particularly, the described embodiments relate to organizing notes, documents, orders, lab results, and other medical information in a computerized database of electronic patient records to improve the efficiency of use.

SUMMARY

One embodiment of the present invention provides a computer system that organizes electronic patient data using a unique data organization scheme. In particular, the computer system creates a customized data presentation that is organized and sorted based on the individual that is viewing the patient's electronic records.

In one embodiment, the computerized system associates each user with a particular "group." Each group can be organized as desired by the users, but typically the users are grouped according to medical specialties. For example, one group of users may practice in medical oncology and another group may practice in radiation oncology. In most situations, the users of the system are also providers that provide care to patients, such as doctors and nurses. Of course, users do not need to be healthcare providers, as staff members, schedulers, and billing coders may also use the system to view patient data even though such users would not be considered providers of healthcare. Nonetheless, for purposes of simplicity, much of the following discussion will assume that the user of the system viewing the healthcare data is also a healthcare provider that may have authored some of that data.

When a user-provider chooses to review the documents or data associated with a patient, the computerized system identifies the group associated with that user-provider and organizes the patient's data in the manner most appropriate for that group. In one implementation, documents are always sorted so that documents authored or otherwise created by the user-provider are presented at the top of the patient data. The next group of documents may relate to documents that were created by other providers in the user-provider's group. Documents created by providers not in the same group as the user would be provided at the bottom of the sorted list of documents.

In another implementation, rules are established for each group that identifies additional documents of special interest. For instance, user-providers in the medical oncology group may find documents created by the radiation oncology group to be more relevant than documents created by other groups. In this case, a user-provider in the medical oncology group would view the following grouping of documents when looking at a patient's data:
documents created by the user-provider,
documents created by other providers in the medical oncology group,
documents created by the radiation oncology group, and then
documents created by all other providers.

Rules can be created to organize documents and data into multiple "special interest" categories, each of which will be presented to the user-provider before documents that don't fit into any of the other categories.

The computerized system can also display a patient's summary data at the top of the data list. This summary data can be extracted from the documents and other data already present in the system. In one embodiment, the summary data identifies when the patient was last seen by the user-provider, and also when the patient was last seen by other providers in the user-provider's group.

DETAILED DESCRIPTION

Figure 1:
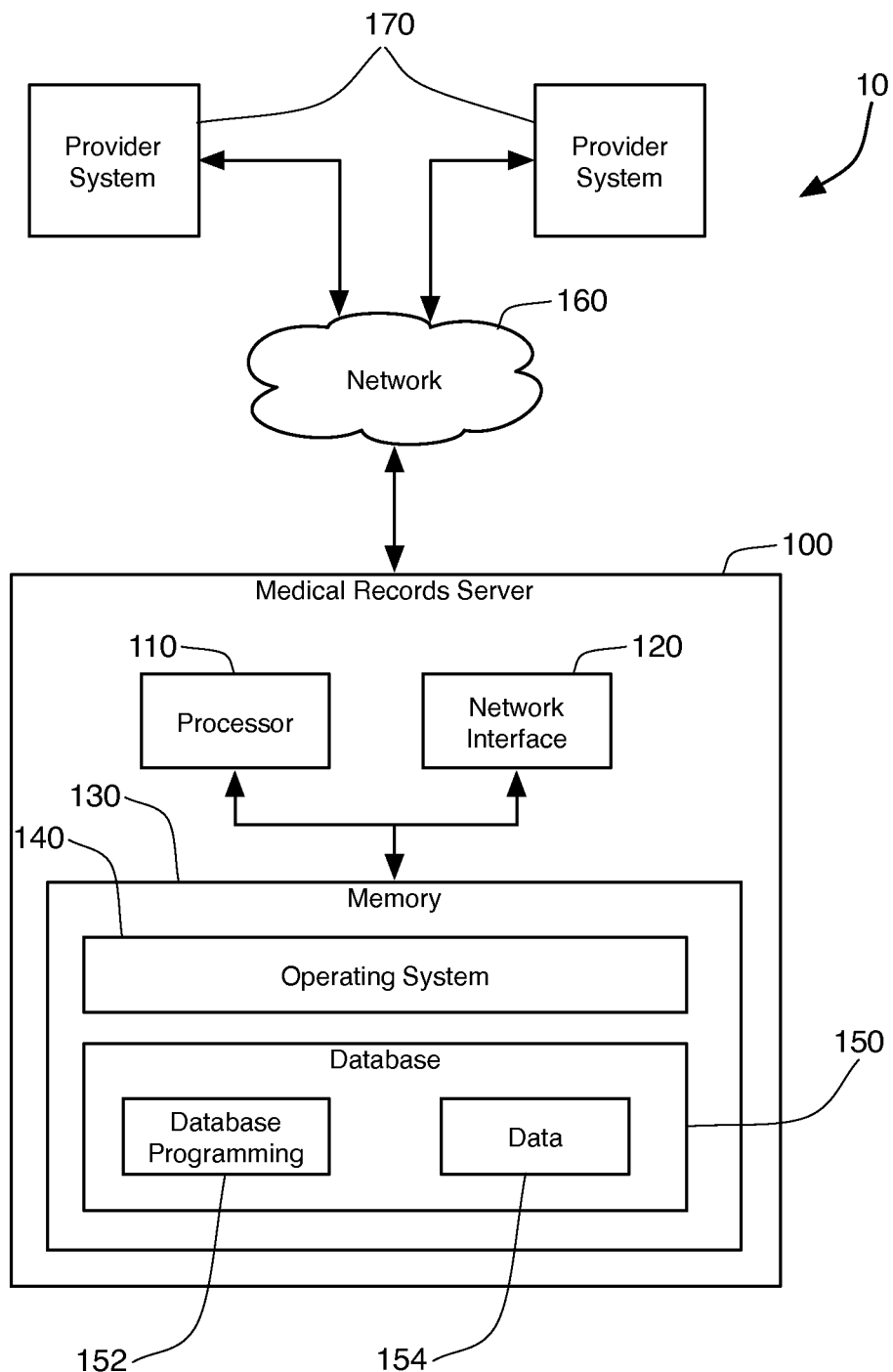
FIG. 1 is a schematic diagram showing one embodiment of the present invention including a computer system.

FIG. 1 shows one embodiment of a medical records system 10 that includes a medical records server 100 accessible by multiple health provider systems 170. Medical records server 100 includes a set of software instructions or operating system 140 stored on a non-volatile, non-transitory, computer-readable memory 130 such as a hard drive or flash memory device. A programmable digital processor 110 such as a general purpose CPU manufactured by Intel Corporation (Mountain View, Calif.) or Advanced Micro Devices, Inc. (Sunnyvale, Calif.) accesses the operating system 140 and executes computer programming in the operating system 140. The operating system 140 typically includes operating system software such as LINUX (available from multiple companies under open source licensing terms) or WINDOWS (available from Microsoft Corporation of Redmond, Wash.). A database 150 also resides on the memory 130. The database 150 contains database programming 152 that can be accessed and executed by the processor 110. Data 154 within the database 150 includes medical records for patients within the healthcare provider systems 170 and information about medical personnel that create and access the medical records. The data 154 also includes orders created for the patients by the medical personnel. The database 150 is stored in the memory 130 as data 154 and related database programming 152. The database programming 152 directs the processor 110 to access, manipulate, update, and report on the database 150 as further described herein. Although FIG. 1 shows the database 150 residing in the same physical memory 130 as the operating system 140 that operates the processor 110, it is not necessary to implement the system 10 in this manner. In other embodiments, the database 150 will reside in external memory. In still further embodiments, the database 150 can be managed and controlled by a separate database server that responds to queries initiated by the medial records server 100 as needed to meet the needs of external devices such as one or more provider systems 170.

Server 100 is further shown with a network interface 120 to communicate with the provider systems 170 over a network 160. In one embodiment, the network 160 is a wide area network such as the Internet or a TCP/IP-based Intranet, and the network interface 120 includes TCP/IP protocol stacks for communicating over the network 160. The network interface 120 may connect to the network 160 wirelessly or through a physical wired connection. Medical records server 100 can be implemented on a single computer with a single processor 110. Alternatively, the server 100 could be implemented using a network of computers all operating according to software instructions.

The provider systems 170 are given access to the data 154 over the network 160. The provider systems 170 could be similar in construction to the server 100, utilizing a general-purpose processor such as those provided by Intel Corporation or Advanced Micro Devices. Alternatively, the provider computer systems 170 could include portable computing devices such as tablet computers or smart phones.

Figure 2:
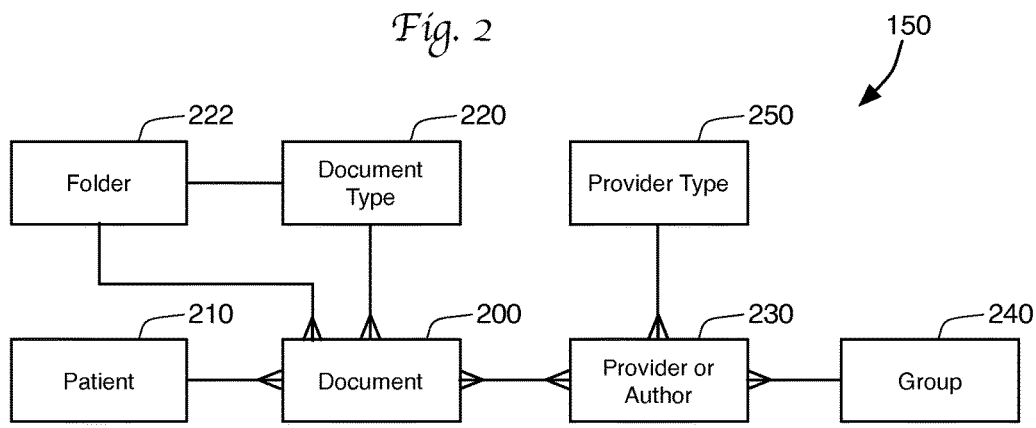
FIG. 2 is a schematic diagram showing the organization of data in the computer system.

FIG. 2 is a schematic diagram of an embodiment in which the server 100 stores the patient data 154 in the structured database 150. The database 150 can be maintained as separate tables in a relational database, or as database objects in an object-oriented database environment. The table or object entities shown in the various figures of this disclosure should not be considered to show actual implementation details of the database 150, since it is well within the scope of the art to implement this type of database using a variety of entity architectures. The entities shown are exemplary, intended to aid in the understanding of the data maintained by the system in this embodiment. It is not even necessary to implement these entities as formal tables or objects, since other database paradigms could also effectively implement these types of data structures. Throughout the remainder of this disclosure, the content and interrelationship of database structures will continue to be explored using these example data structures, but these structures should not be considered to limit the way in which these databases can be constructed.

FIG. 2 shows the database 150 with tables or objects for a document 200, a patient 210, a document type 220 and folder 222, a provider or author 230, a group 240, and a provider type 250. Relationships (or "associations") between the database entities are represented in FIG. 2 using crow's foot notation. Associations or relationships between the database entities shown in FIG. 2 can be implemented through a variety of known database techniques, such as through the use of foreign key fields and associative tables in a relational database model.

The database 150 is particularly helpful to track and organize documents 200 that contain a report, image, graph, notes, or other information about a single patient 210 written or created by a health service provider (or some other author) 230. In most circumstances, the document 210 will be generated in connection with a particular clinical event (such as an appointment, procedure, or test) having an event date. Thus, in the preferred embodiment, when the content and date for a document 200 is input into the database 150, the document 200 is immediately associated with a single patient database record 210 and a provider (or author) database record 230. In most cases, a document 200 will have a single author/provider 230, although the database 150 is designed to allow each document 200 to have multiple authors 230 associated with it. In addition, every document database entity 200 will have a particular document type 220 assigned to that document 200. The document type 220 describes the type of document that is being tracked by the document database entity 200. Example document types could include transcribed documents, radiology results, and nutrition documents. FIG. 2 shows that a single folder 222 is associated with a single document type 220, and vice versa. As explained below, the folder database entity 222 can be used to organize the documents 200 by document type 220. In an alternative embodiment, the folder database entity 222 and the document type database entity 220 would be merged into a single entity. In other embodiments, document types 220 would not be implemented as a separate database entity, but merely as a field entry in a document database entity 200.

Providers 230 may include doctors, nurses, or other medical professionals authorized to create or view medical documents 200 for patients 210 in the system 10. Each provider 230 is associated with a provider type 250. The provider type 250 may indicate the provider 230's profession such as nurse, doctor, etc. Each provider 230 is also assigned a group 240 composed of multiple providers 230. A particular group 240 may be composed of providers 230 with a variety of provider types 250. Groups 240 are preferably categorizations of medical specialties and subspecialties such as primary care, medical oncology, radiation oncology, general radiology, orthopedics, surgical groups, and other such health care provider categorizations.

FIG. 2 uses the term "document" to describe the type of data that is managed and organized in this database 150. In one embodiment, the database 150 is limited to traditional "documents" that are created by the authors/providers 230. However, the methods and systems described herein apply equally to other types of data. For example, the data that is sorted and presented by the computerized system 100 can be documents created by the user-providers 230, patient orders, lab data and results, radiology studies, imaging data, diagnostic data, and other machine-generated and provider-generated medical data that may be relevant to a provider that is providing care to a patient.

Figure 3:
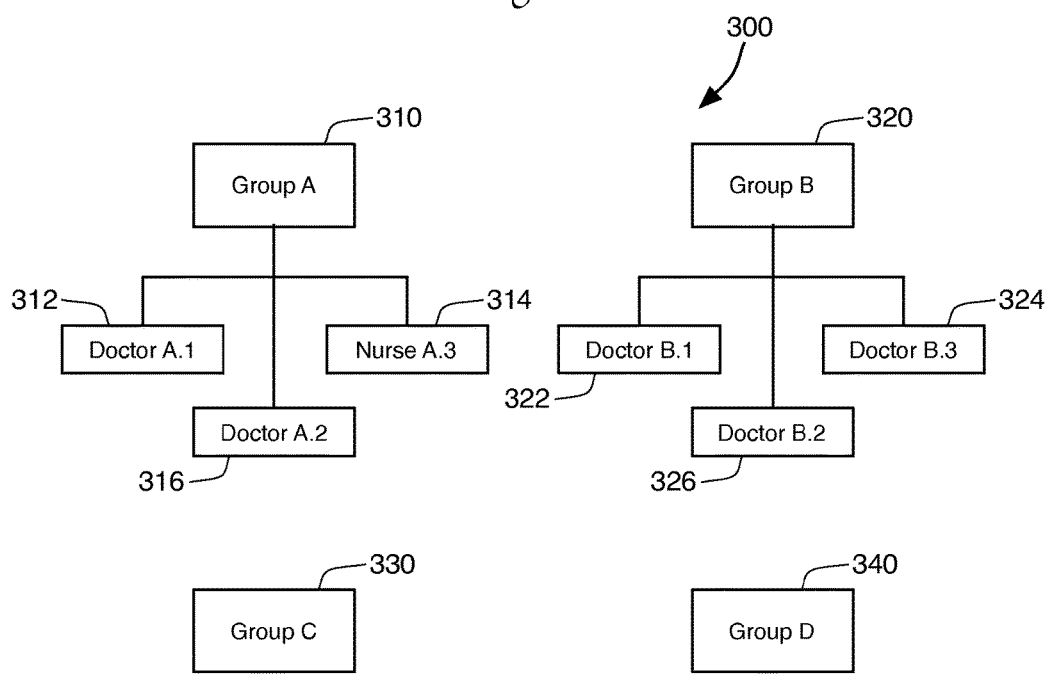
FIG. 3 is a schematic diagram showing organization of providers and groups as embodied in the computer system.

FIG. 3 shows a schematic diagram of the composition of provider groups 240 within the database 150. FIG. 3 shows four groups 310, 320, 330, and 340. In the preferred embodiment, each group 310-340 indicates the medical specialty of the professionals within that group. Group A (310) is composed of medical professionals working in a particular specialty, such as obstetrics, and includes Doctor A.1 (312), Nurse A.3 (314), and Doctor A.2 (316). In the example of FIG. 3, Doctor A.1 312 and Doctor A.2 316 may have the same provider type 250, while Nurse A.3 314 may have a different provider type 250. However, all of these providers 312-316 within Group A 310 would be part of the same medical group. FIG. 3 also shows Group B (320) having medical professionals Doctor B.1 (322), Doctor B.2 (324), and Doctor B.3 (326). Group C (330) and Group D (340) are similar to Groups A 310 and B 320, although the providers 230 that belong to these groups 330, 340 are not explicitly shown in FIG. 3.

Figure 4:
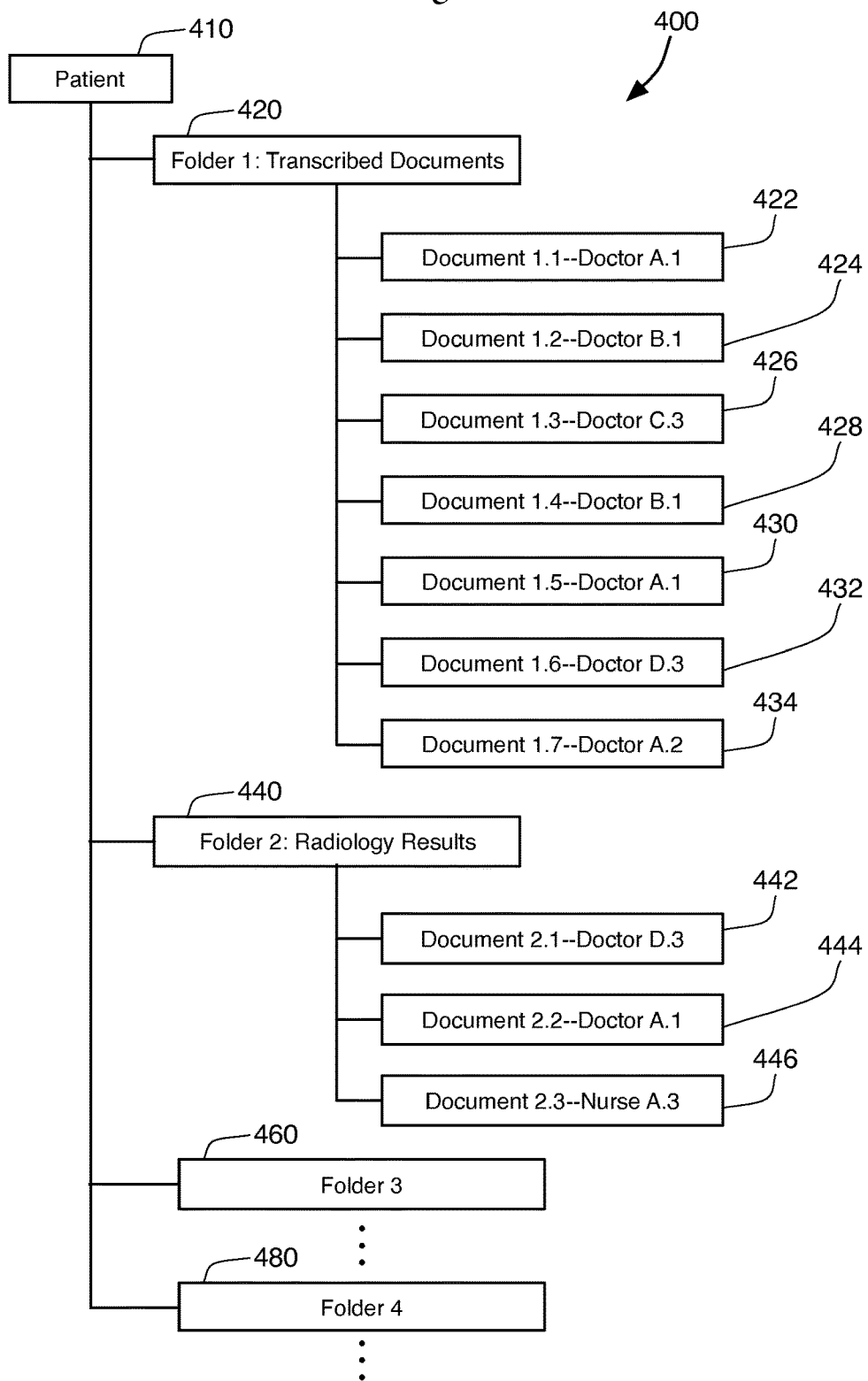
FIG. 4 is a schematic diagram illustrating one embodiment of document organization that can be implemented on the computer system.

FIG. 4 is a schematic diagram showing a document organization scheme 400 that categorizes documents 200 into folders 222 (or document types 220) using the computerized database 150. A particular patient 410 is shown associated with a plurality of documents. As shown in FIG. 4, documents 422, 424, 426, 428, 430, 432, and 434 are associated with Folder 420, which has a document type of "Transcribed Documents." Each of the documents 422-434 is associated with a health care provider that created the particular document. For example, document 1.1 422 is associated with Doctor A.1 312, document 1.2 424 is associated with Doctor B.1 322, etc. The documents 422-434 are similar in that they are documents transcribed for doctors for the particular patient 410. However, the contents of the documents 422-434 are not necessarily related. The individual documents 422-434 may relate to different health conditions or different office visits for the single patient 410.

Folder 440 is associated with the document type "Radiology Results." Documents 442, 222, and 446 are categorized under this document type. Folders 460 and 480 may each contain additional documents for patient 410.

Figure 5:
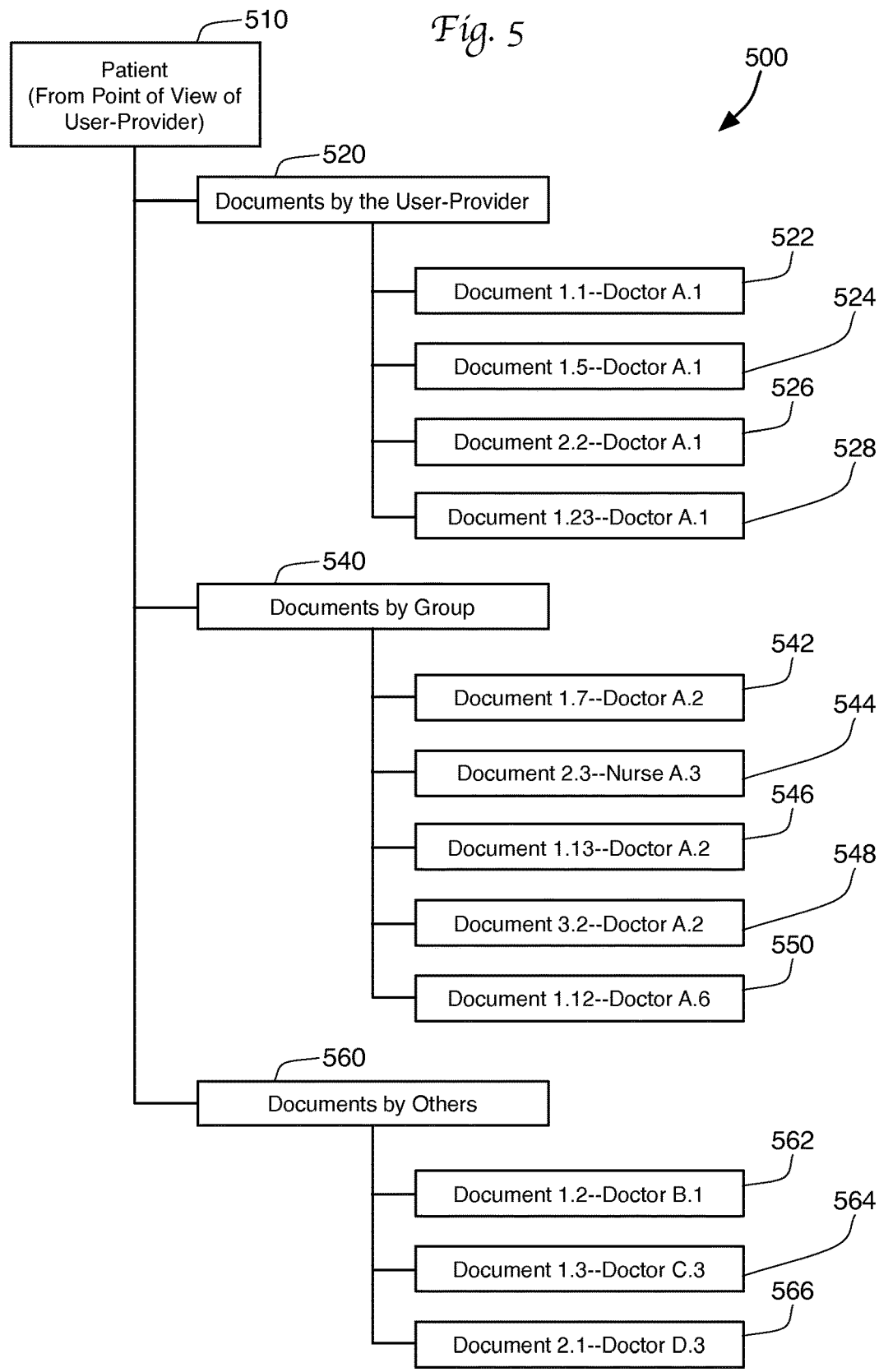
FIG. 5 is a schematic diagram illustrating a second, improved embodiment of document organization that can be implemented on the computer system.

FIG. 5 shows a second, improved embodiment of a document organization scheme 500 that can be implemented by system 10. In FIG. 5, documents 200 for a patient 210 are not organized based on the folder 222 that the document 200 is associated with in the database 150. Instead, documents 200 for a particular patient 510 are organized dynamically for each medical professional using the system 10. A single medical professional viewing a patient's records is referred to herein as the "User-Provider." The document organization scheme 500 can be used in the system 10 described in FIGS. 1-3 without changing the basic structure of the database 150.

In FIG. 5, the User-Provider is Doctor A.1 (312). In the document organization scheme 500, the User-Provider has a grouping of documents (called a "document category") 520 of documents 522-528 created by the User-Provider. Documents 522, 524, 526, and 528 are each associated with User-Provider (Doctor A.1), but the documents may have different document types. For example, documents 522, 524, and 528 may have a document type "Transcribed Documents," while document 526 has a document type "Radiology Results." A second document category 540 contains a selection of documents 542, 544, 546, 548, and 550 that are associated with medical professionals that belong in database 150 to the same group as the User-Provider. As Doctor A.1 is associated with Group A 310, this category 540 shows documents 542-550 that were authored by other providers who are also in Group A 310. A third category of documents 560 contains documents 562, 564, and 566 that were created by medical professionals in other groups for the patient 510.

As mentioned above, some documents 200 in the database 150 are associated with multiple authors 230. There are a variety of ways of organizing multi-author documents in organization scheme 500. In one embodiment, a multi-authored document is presented only a single time in the entire organizational scheme 500, typically in the highest ranked (top-most) document category for any of the document's authors. In other embodiments, the document will appear multiple times, once in each document category that was appropriate for any of the document's authors. It is possible that documents with multiple authors will be highlighted or otherwise identified in the organization scheme 500 so that the user viewing the presented documents will immediately recognize that the document has multiple authors (and therefore may appear at multiple locations in organization scheme 500).

The key distinction between organization scheme 400 and organization scheme 500 is that the later scheme dynamically reorganizes the user documents based on the user that is current viewing the documents. In scheme 400, every provider using the system will see the same organization of documents. In order to find documents relevant to that user, the user will have to search the entire hierarchy 400 of documents. With scheme 500, every provider will see a customized organization of documents in which the documents that are likely to be most relevant to the user are presented first in the hierarchy 500. It is estimated that three to five minutes of the User-Provider's time can be saved for each twenty minute patient appointment by using scheme 500 as opposed to scheme 400.

Figure 6:
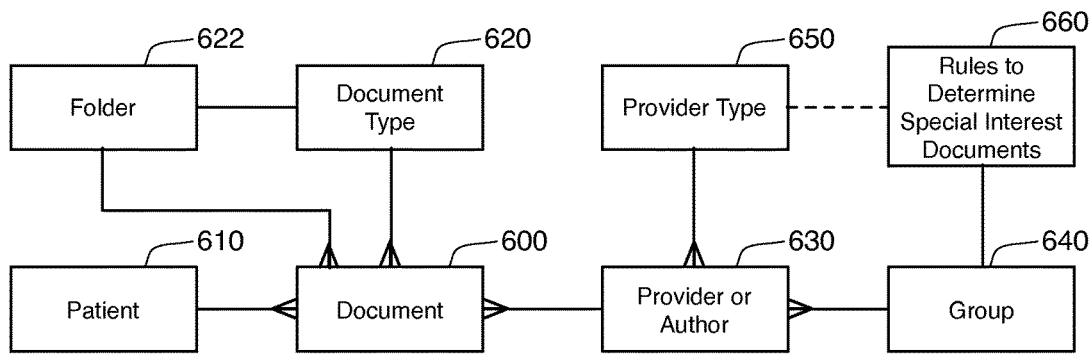
FIG. 6 is a schematic diagram showing a second organization of data in the computer system.

FIG. 6 shows a second embodiment of a database structure as embodied in the computer system. FIG. 6 is similar to FIG. 2, in that a plurality of documents 600 are associated with a patient 610, a folder 622, a document type 620, and a provider 630. Each provider 630 has a provider type 650. A group 640 is associated with a plurality of providers 630. In addition, the embodiment of FIG. 6 provides a set of rules 660 in the database to determine special interest documents 600 that are sub-categorized for viewing according to the User-Provider 630 that is viewing the documents 600.

Figure 7:
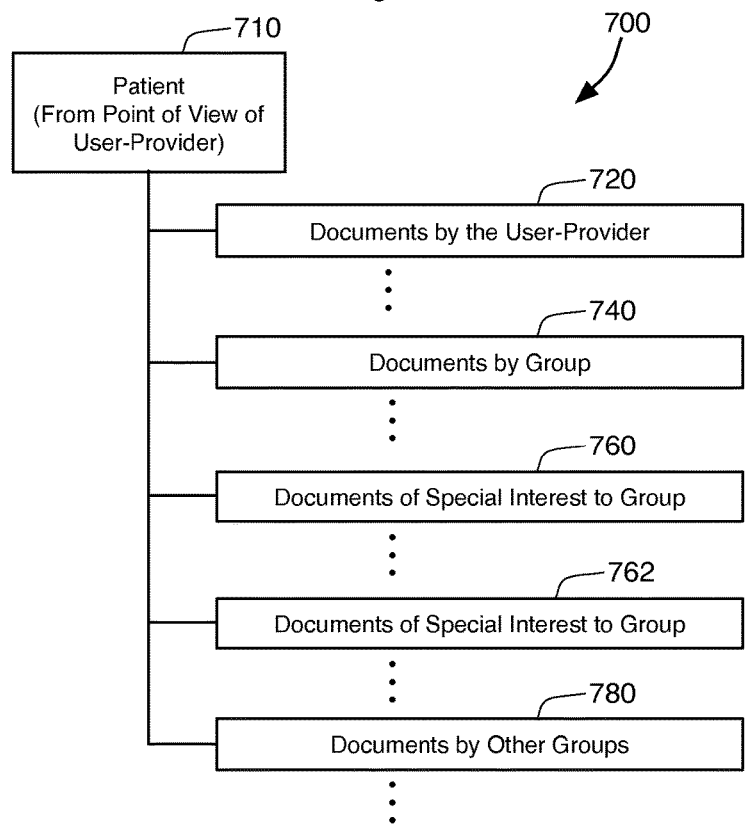
FIG. 7 is a schematic diagram illustrating a third, improved embodiment of document organization that can be implemented on the computer system.

FIG. 7 shows a third, improved embodiment of a document organization scheme 700 that can be implemented on the computer system 10. A patient 710's medical documents are organized based on point of view of the provider 630 that is viewing the documents 600 (the User-Provider). Documents by the User-Provider are organized under category 720. Documents by other medical providers in the User-Provider's group are organized under category 740. After the documents for patient 710 are organized by sub-categories 720 and 740, other documents created by providers not within the User-Provider's group may still be of special interest to the User-Provider. For example, the User-Provider could be a member of Group A, and providers in Group A may work very closely with providers in Group C. In particular, documents of a certain types 620 by providers in Group C may be very important to providers in Group A. The rules 660 in the database 150 described above help to identify these types of documents and create one or more sub-categories 760, 762 of documents of "Special Interest." In this case, the rules established two different types of documents 760, 762 that would be of interest to the User-Provider, and therefore grouped these documents separately from other documents 780. Finally, documents by medical providers in other groups are organized under category 780. This category includes those documents 600 created by providers 630 in groups 640 other than the group of the User-Provider. In addition, this category excludes those documents 600 that were included in the documents of special interest categories 760, 762 created by rules 660.

Figure 8:
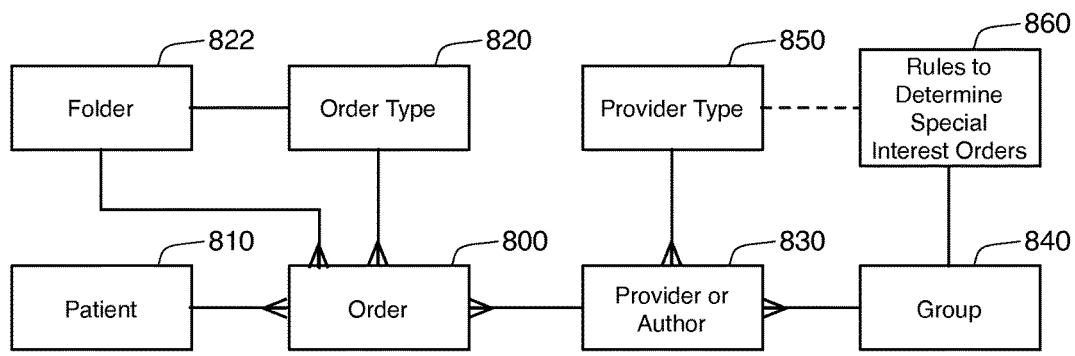
FIG. 8 is a schematic diagram showing a third organization of data in the computer system, with this data relating to patient orders.

FIG. 8 is a schematic diagram showing an organization of patient orders 800 in the computer system. Patient orders 800 may include laboratory orders, imaging orders, pharmaceutical orders, admission orders, etc. Patient orders 800 are organized in database 150 in a manner very similar to the documents 200, 600 of FIGS. 2 and 6, respectively. One or more patient orders 800 for a patient 810 are associated in the database 150 with a folder 822 and an order type 820. The order 800 is also associated with the provider 830 that created the order 800. Each provider 830 in the system is associated with a provider type 850 and a group 840. The system also contains rules 860 to determine special interest orders for particular groups or provider types.

Figure 9:
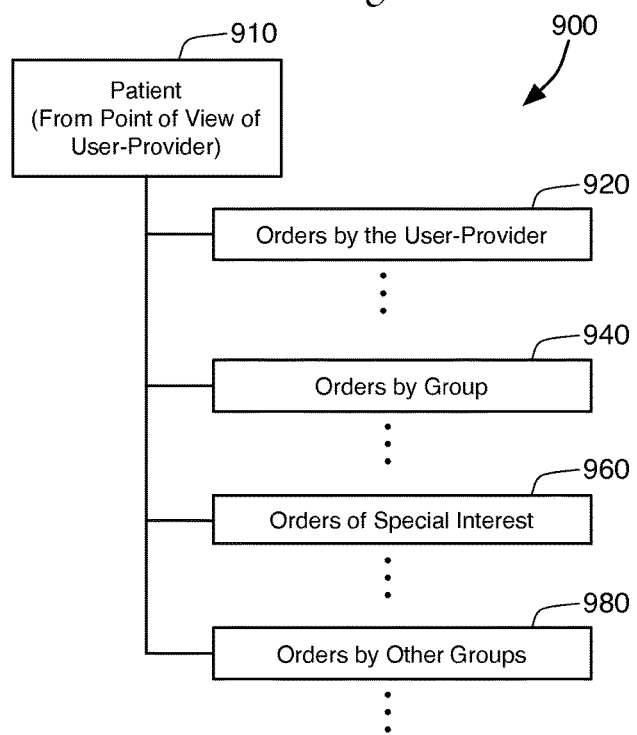
FIG. 9 is a schematic diagram illustrating an embodiment of order organization that can be implemented on the computer system.

FIG. 9 is a schematic diagram illustrating an embodiment of an order organization scheme 900 that can be implemented on the computer system. A plurality of patient orders for a patient 910 are grouped from the point of view of a provider 830 that is viewing the orders 800 (the User-Provider). Multiple patient orders 800 are created by one or more healthcare providers 830 for the selected patient 910. In the order organization scheme 900, orders by the User-Provider are placed in a first category 920. The orders in the category 920 are created by the User-Provider and associated with the User-Provider in the database 150 maintained through the medical records server 100. A second category 940 includes orders by healthcare providers by other professionals in the User-Provider's group 840. A third category 960 includes orders by healthcare providers not in the User-Provider's group that were identified by the rules 860 stored in the computer system 100. Finally, orders by healthcare providers in other groups that are not included in category 960 are provided in a fourth category 980.

Figure 10:
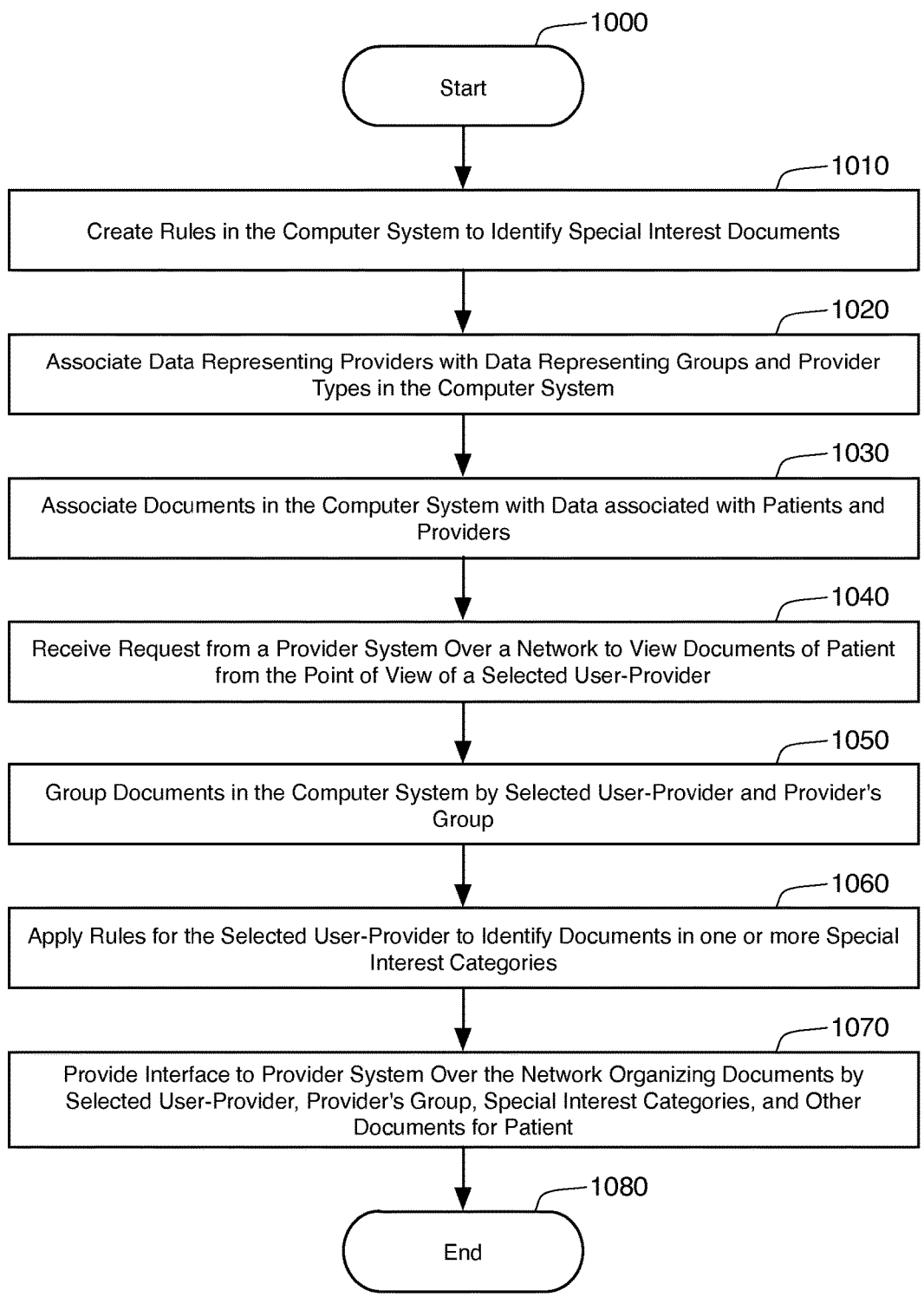
FIG. 10 is a flow chart showing a computerized method for performing one embodiment of the present invention.

FIG. 10 is a flow chart showing a computerized method 1000 for performing one embodiment of the present invention. The method 1000 may be performed in the medical records server 100 shown in FIG. 1. Although the method is presented as a series of steps, the steps may be performed in any order and in any combination, and steps could be added or omitted.

In step 1010, rules 660 are created in the computer system 10 (such as in medical records server 100) to identify documents 600 of special interest to certain providers 630. These rules are also described in connection with FIG. 14 below. In step 1020, data representing providers 630 are associated with data representing groups 640, and with data representing provider types 650. In step 1030, documents 600 in the computer system are associated with patients 610 and providers 630. This is typically accomplished whenever a document 600 is added to the database 150. In most cases, each document 600 is associated with a single patient 610 and a single provider 630. In step 1040, a request to view documents 600 for a patient 610 is received from a provider system 170 over the network 160. The request includes a request to view the documents 600 for a particular patient 610 from the point of view of a selected User-Provider 630. In step 1050, a grouping of documents 600 is performed in the computer system based on the selected User-Provider and the User-Provider's group. In the exemplary embodiment provided in FIG. 7, a first grouping of a category 720 of documents 600 from the point of view of the User-Provider is performed. This first document category 720 includes those documents 600 directly associated with the User Provider. A second document category 740 is then created by identifying documents 600 created by providers 630 that are in the same group 640 as the User-Provider. In step 1060, rules 660 are selected based on the User-Provider's group 640 (and, in some embodiments, the User-Provider's provider type 650). The identified rules are then applied to remaining documents 600 for the patient 610 to identify documents 600 in one or more special interest categories defined by the rules 660.

In step 1070, data to create an interface is provided by the medical records server 100 to the Provider 170 over the network 160. The interface organizes documents by a selected User-Provider 720, the provider's group 740, the special interest categories 760, and all other documents 780 for the patient. In the preferred embodiment, the interface will display only those categories 720, 740, 760, 780 that contain documents for the selected patient so as to avoid displaying empty categories 720, 740, 760, 780. In addition, the display step 1070 can alter the display of individual documents if desired by the user. For example, in some embodiments each document 600 can have a separate status. A transcribed document, for instance, could have a preliminary status after the document has been transcribed but not confirmed by the provider, and a confirmed status after the document has been confirmed by the associated provider. Unconfirmed documents could be presented in the interface in highlighted or emphasized fashion to ensure that users of the system 10 would identify the documents as unconfirmed. The method ends at step 1080.

Figure 11:
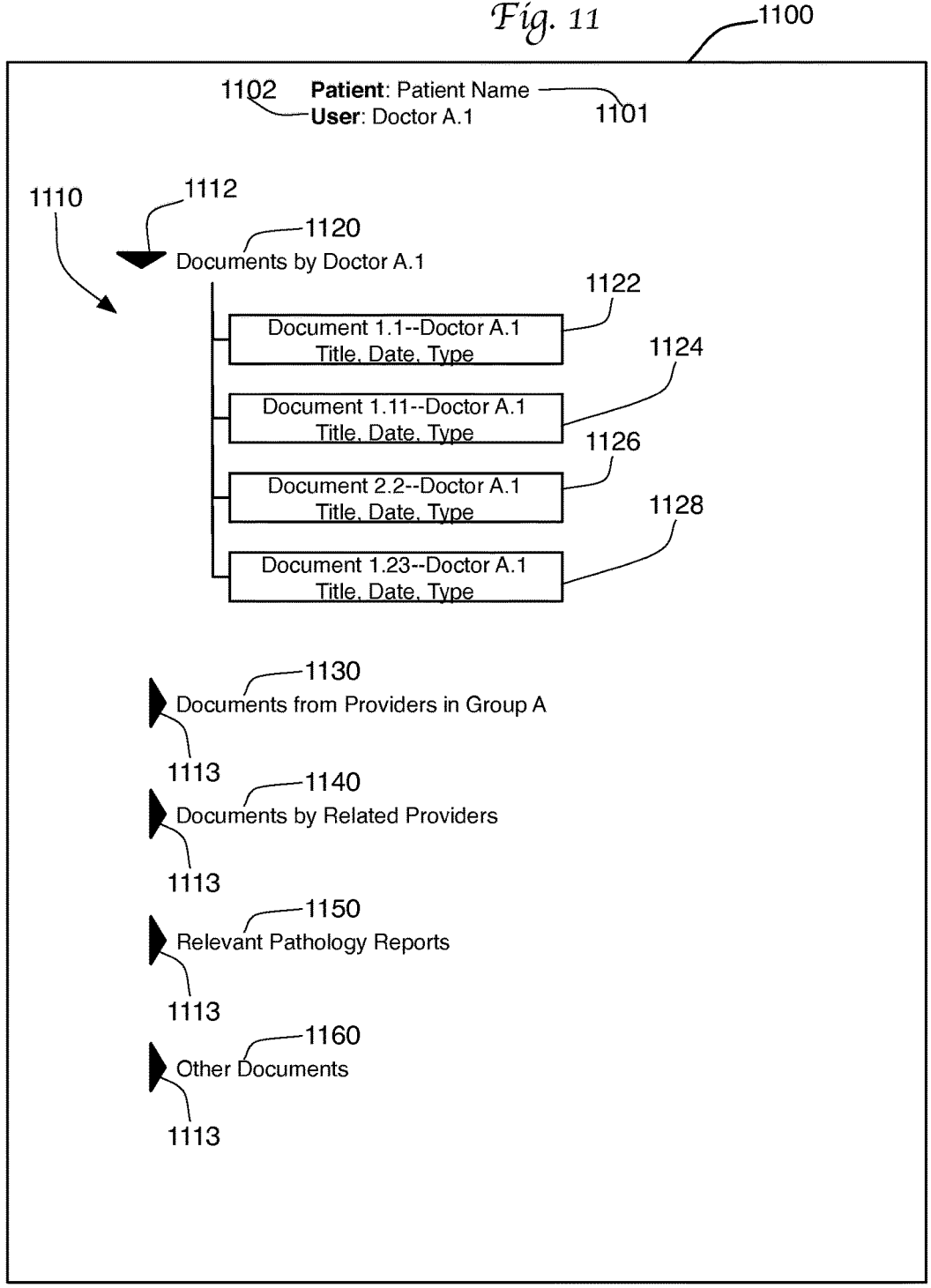
FIG. 11 is a schematic diagram showing a user interface generated for a provider system to display organized documents.

FIG. 11 is a schematic diagram showing a graphical user interface (GUI) 1100 generated for a provider system 170 to display organized documents for a user 1101. The GUI 1100 may be implemented on a general-purpose computer having a computer processor, a computer memory, software logic residing on the memory and executed by the computer processor, and a computer monitor to display the GUI 1100. The GUI 1100 could also be implemented on a mobile device or smartphone using an app programmed for that device. Although the GUI is generated at the provider system 170, the GUI utilizes data, and in most cases formatting instructions, provided by the medical records server 100 over network 160.

The interface 1100 presents documents for a particular patient 1101 to a particular User-Provider 1102. These parties 1101, 1102 are identified at the top of the interface 10 shown in FIG. 11. The interface 1100 divides the documents 1110 for that patient 1100 into a User-Provider document category 1120, a group providers document category 1130, a related providers document category 1140, a pathology reports category 1150, and an other documents category 1160. In this case, the rules 660 for the provider's group 640 and type 650 identify two documents subcategories of special interest, namely the "Related Providers" subcategory 1140 and the "Relevant Pathology Reports" category 1150. Documents in the category 1120 are presented in the GUI as an indented list of documents 1122, 1124, 1126, and 1128. Toggle icons 1112 and 1113 may be provided in the GUI 1100. The toggle icon 1112 is displayed when the documents in a particular category, such as category 1120, are listed on the interface 1100. The toggle icon 1112 could also be implemented as a "drop-down" list. The toggle icon 1113 is displayed when documents in a particular category, such as category 1160, are not displayed on the interface 1100. The user can choose to view the documents 1110 for a hidden category 1130, 1140, 1150, 1160 by clicking on toggle icon 1113, which will cause the interface 1100 to display the documents 1110 for that category 1130, 1140, 1150, 1160 and change icon 1113 to icon 1112. Similarly, clicking on icon 1112 will cause the displayed documents 1122-1128 to be hidden and change icon 1112 to look like icon 1113.

In the embodiment shown in FIG. 11, the documents provided in category 1140 and category 1150 are special interest documents to the user 1102 viewing the GUI 1100. The special interest documents are determined based on rules 660 provided in the database 150. In this case, the Doctor A.1 has particular documents in category 1140 that are created by healthcare providers outside of the Doctor A.1's group, but that are still relevant to the Doctor A.1. Documents in the category 1150 are pathology reports for the patient 1101 that the rules 660 indicated should be treated as being a special category of documents for this User Provider 1102.

Any documents 1110 for the patient 1101 that are not found in the other subcategories 1120-1150 are found in category 1160. These documents remain viewable by the Doctor A.1, but are placed at the bottom of interface 1100 because such documents are less likely to be relevant to the User-Provider's care of the patient 1101.

Figure 12:
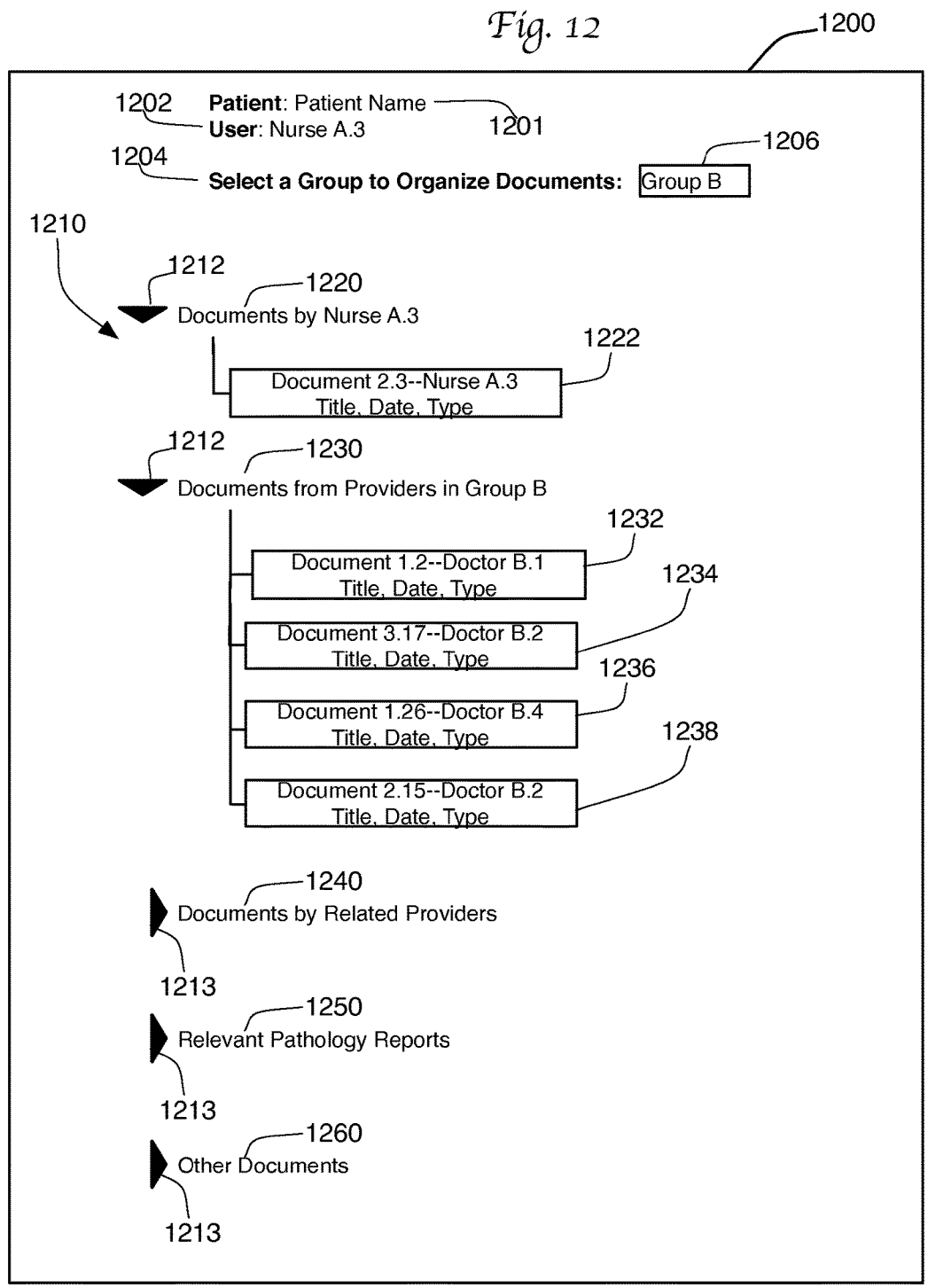
FIG. 12 is a schematic diagram showing a second user interface generated for the provider system to display organized documents that allows user selection of group organization.

FIG. 12 is a schematic diagram showing a second graphical user interface (GUI) 1200 generated for the provider system 170. This interface 1200 allows user 1202 to select the group "point of view" through which the documents should be displayed. This allows a user to view documents for a particular patient from the point of view of a group that is different than the User-Provider's own group. In FIG. 12, the interface 1200 is being used by Nurse A.3, as shown at user interface element 1202. In this example, the Nurse A.3 belongs to Group A in the database 150, but wishes to view the documents for patient 1201 from the point of view of Group B. This may be because Nurse A.3 belongs to Group A, but is temporarily assigned to work with and assist other providers in Group B. The interface 1200 allows the Nurse A.3 to make a selection 1204 of a particular group 1206, which causes the interface 1200 to organize and display the documents 1210 from the point of view of Group B.

As seen in FIG. 12, interface 1200 continues to prioritize documents 1222 created by Nurse A.3 (the User-Provider that is viewing the documents) by placing these documents in the first displayed category 1220. In an alternative embodiment, the category 1220 would not be displayed whenever a view-by group 1206 is selected that is different from the group of the provider 1202 that is viewing the interface 1200.

The second document category 1230 shows documents for the patient 1201 created by providers in the group 1206 selected by the user (in this case, Group B). This is true even though the current user 1202 (Nurse A.3) is assigned within the database to Group A. Documents 1232, 1234, 1236, and 1238 were created by healthcare providers in Group B and are therefore shown in category 1230. Toggle icon 1212 is displayed when documents in a particular category are displayed.

Category 1240 and category 1250 contain documents of special interest to the user 1202 from the point of view of the selected group 1206. In FIG. 12, the documents in subcategories 1240 and 1250 are determined based on rules 660 in the patient records database. These rules 660 are associated with the provider type for the current user 1202, but are associated with the group selected at user interface element 1206 (Group B) rather than the group associated with the current user 1202 (which would be Group A). Toggle icon 1213 is displayed when documents in a particular category are hidden. Other documents for the patient 1201 are provided under category 1260.

Figure 13:
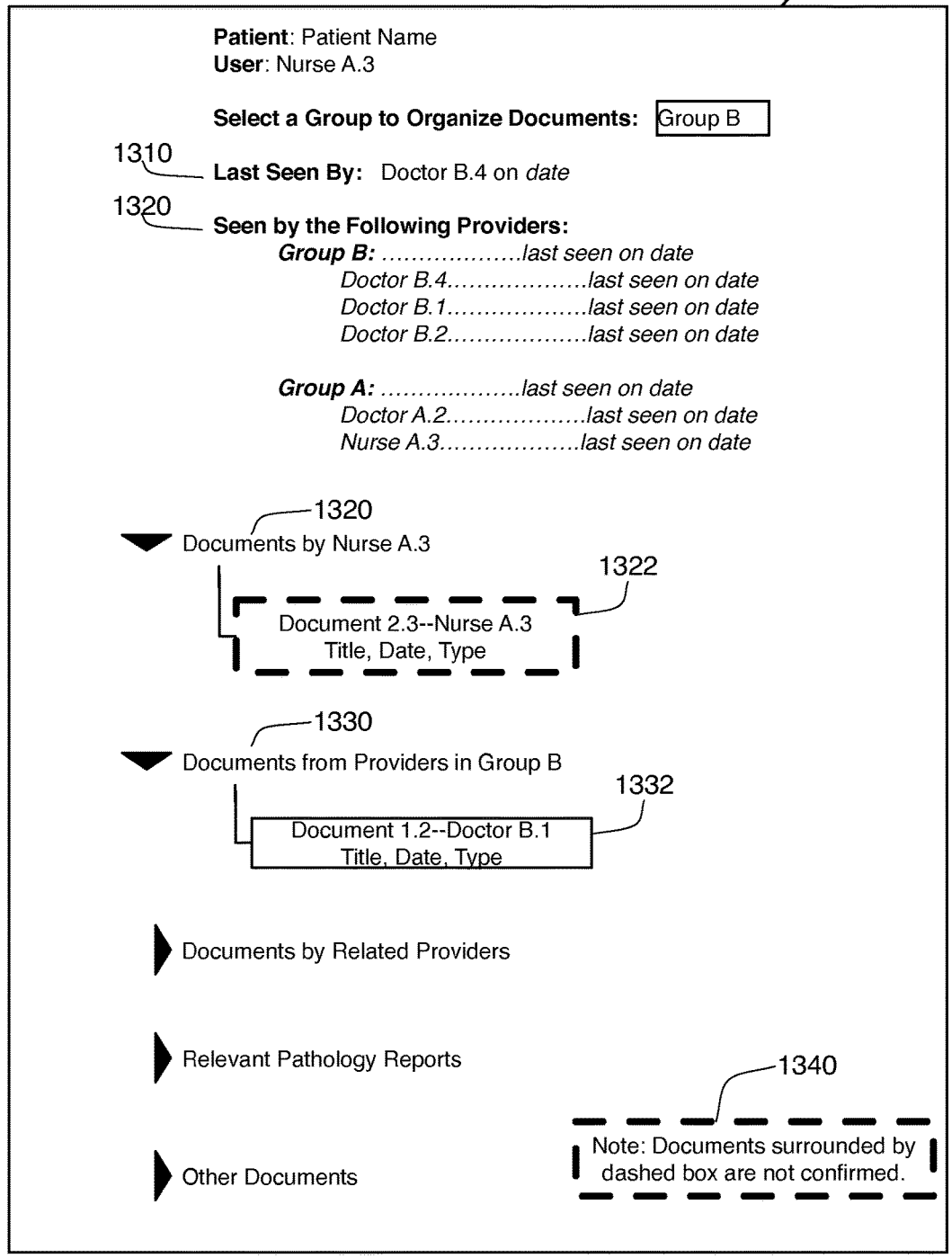
FIG. 13 is a schematic diagram showing a third user interface generated for the provider system to display organized documents.

Interface 1300 shown in FIG. 13 is similar to interface 1200, but includes summary data 1310, 1320 at the top of the interface that is derived from the documents 200 in the database 150. At location 1310, the interface 1300 determines the last date at which the patient was seen by any provider that uses the system 10. This can be extremely helpful to physicians who are trying to understand a patient's health history as quickly as possible. This information 1310 could be linked to the document(s) 200 in the database that were associated with this date. At location 1320, the interface 1300 lists all of the providers that have seen this patient and the last date on which the identified provider saw the patient. The list 1320 shown in FIG. 13 has been sorted by group (group B first, and then other groups) and then provider type 250 (physicians then nurses, for example). Other sort orders would be possible, such as by first sorting the groups alphabetically, and then by sorting the providers within each group in reverse chronological order based on the date each provider last saw this patient. Again, each entry in the list could be linked to document(s) 200 that are associated with the last entry made by that provider.

Finally, FIG. 13 shows that document 1322 has been highlighted so as to distinguish this document 1322 from other documents such as document 1332. In FIG. 13, a thick, dashed box surrounds the document 1322 while un-highlighted document 1332 has only a thin, solid box. In other embodiments, the highlighted document 1322 can be presented in a different font or font color, or with a different background color. Regardless of the method of highlighting selected, the goal is to differentiate this document 1322 from other documents. A key 1340 on this interface 1300 explains the significance of this highlighting. In FIG. 13, the highlighting indicated that the content of the document 1332 has not been confirmed by the author (in this case, Nurse A.3). In some embodiments, multiple types of highlighting can be used within a single interface 1300, with each different type having a different meaning as indicated by the key 1340. The highlighting of documents can be used for other purposes as well, such as to indicate which documents are less than three months old, or which documents are more than three years old.

The highlighting or emphasizing of document having a certain age is very useful in a variety of circumstances. For instance, many insurance companies allow providers to bill for "new client" visits even if the provider had previously seen the patient, as long as the most recent visit is at least three years in the past. A billing staff member working for a particular group could access interface 1300 and view the patient records from the point of view of their group. If the patient had been seen by a provider in that group more than three years earlier, the billing staff member could immediately recognize that that visit (associated with a particular document 1322, 1332) was more than three-years in the past based on the highlighting or emphasis shown in the interface 1300. This staff member would then know that the most recent patient visit could be billed as a new client visit.

In another billing context, some insurance companies provide a flat reimbursement for particular procedures, which includes all visits between the patient and the provider within a "global period." For example, a certain type of operation may be reimbursed at a particular rate, which must include all patient visits within a set 90-day global period. By managing the highlighting displayed in interface 1300, documents associated with the operation during the global period could be highlighted. This allows a billing staff member to immediately recognize that patient visits during this time period should not be separately billed to the insurance company. If the patient is being seen for a condition unrelated to the surgery, the insurance company will reimburse for the visit but only if certain billing code modifiers are included in the reimbursement request. The billing staff member will recognize that this situation applies based on the highlighting shown in interface 1300, and will then know that additional modifiers must be included in the insurance paperwork.

Figure 14:
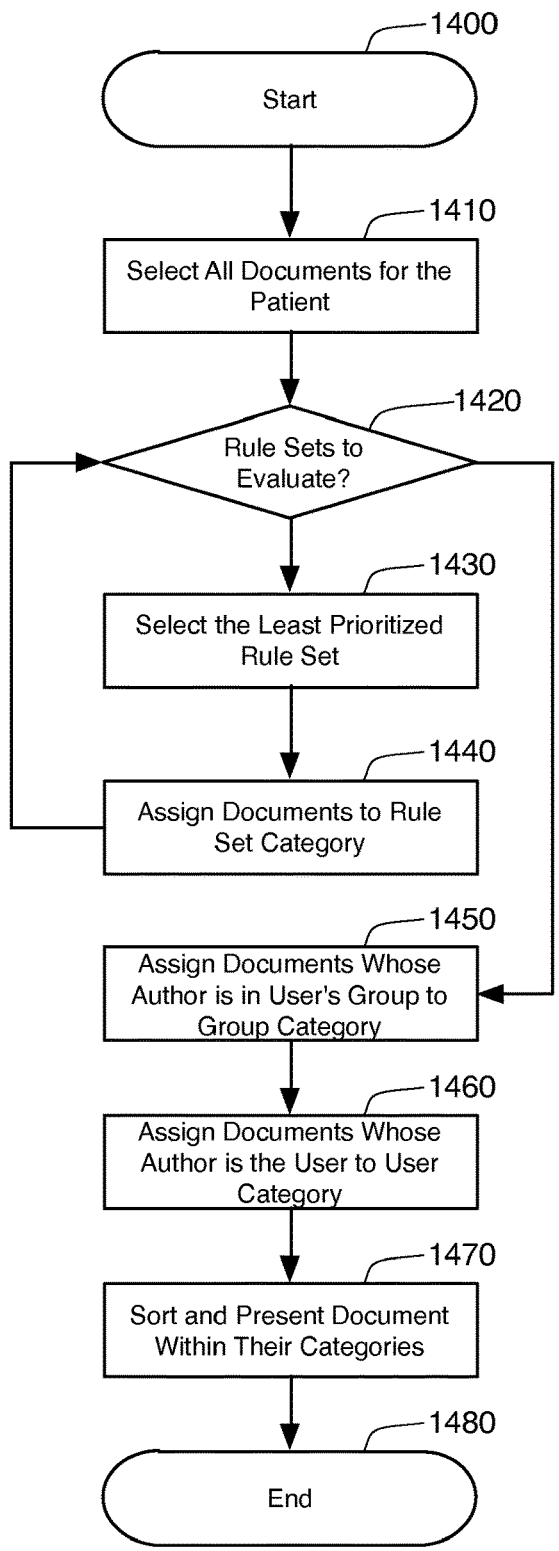
FIG. 14 is a flow chart showing a computerized method for applying rules within one embodiment of the present invention.

FIG. 14 shows a flow chart for a method 1400 of categorizing documents 600 for a patient 610 as shown in interface 1100. The method 1400 starts at step 1410 by identifying every document 600 associated with the patient 610, in this case patient 1101 shown on the top of interface 1100 in FIG. 11.

At step 1420, the method 1400 determines whether there are any rules 660 associated with the User-Provider 630 that is viewing these documents 600 (which is Doctor A.1 1102 in FIG. 11). These rules 660 can be the same for all providers 630 within the provider's group 640, so that every user 630 within the group 640 is associated with the same rules 660. Alternatively, the rules 660 can be associated with both the group 640 and the provider type 650, so that each provider type 650 within a group 640 could have a different set of rules 660. In this latter embodiment, nurses within a particular group (such as obstetrics) could see a different set of categories in the presentation of documents for a patient than doctors within that same group.

If step 1420 determines that there are rules associated with the user 630, step 1430 selects the least prioritized rule set that has not yet been evaluated. In the preferred embodiment, each rule set comprises a set of rules 660 that categorizes documents into a single category. For instance, one rule may indicate that documents 600 with a document type 620 of "cytology report" should be assigned to the "Relevant Pathology Reports" category 1150. A second and third rule 660 may indicate that documents 600 with a document type 620 of "surgical pathology report" and "pathology report", respectively, should also be assigned to the Relevant Pathology Reports category 1150. These three rules 660 constitute a rule set, as they all assign documents 600 to the same document category 1150. Different rule sets may have different priorities, which determine the order in which the resultant report categories 1140, 1150 are presented in the interface 1100. In FIG. 11, the "Relevant Pathology Reports" category 1150 had a lower priority than the "Documents by Related Providers" category 1140, and therefore appears below that category.

After step 1430 determines the least prioritized rule set that has not yet been evaluated, step 1440 applies the rules 660 within the selected rule set to all of the documents 600 that were identified in step 1410. If a rule 660 applies to a particular document 600, that document 600 is assigned to the special interest category 1140, 1150 defined by the rule set. Afterwards, the method 1400 returns to step 1420 to determine if any more rules sets remain to be evaluated. If so, steps 1430 and 1440 repeat for this next rule set.

When all the relevant rule sets have been applied to the documents 600, step 1450 then examines all of the documents 600 identified in step 1410 to find documents 600 whose author 630 is in the same group 640 as the user currently viewing the documents 600 (User-Provider 1102 in FIG. 11). Thus, if the current user 1102 is Doctor A.1 who is associated within the database 150 with Group A, step 1450 will find all documents 600 whose author 630 is also in Group A. These documents 600 are then assigned to the Documents from Providers category 1130. Next, step 1460 assigns those documents 600 whose author 630 is the same as the User-Provider 1102 to the Documents by Current User category 1120. Documents 600 that are found in step 1410 but not assigned in steps 1440-1460 will be considered part of the Other Documents category 1160.

It is possible that a single document 600 will be assigned by method 1400 multiple times to different categories 1120, 1130, 1140, or 1150. In the preferred embodiment, each new assignment changes the category assignment for that document 600. For instance, Document 2.2 1126 may be assigned by the rules 660 to the Relevant Pathology Reports category 1150, then assigned to the Documents from Providers in Group A category 1130, and finally to the Documents by Doctor A.1 category 1120. Because only one category 1120, 1130, 1140, or 1150 is assigned to the document 1126 at a time, each new assignment changes the document category for that document 1126. By assigning the categories 1120, 1130, 1140, or 1150 in the order set forth in FIG. 14, the document 1124 is sure to be presented in the highest applicable category 1120, 1130, 1140, 1150, or 1160. Finally, at step 1470, the documents are sorted and presented in the appropriate document category 1120, 1130, 1140, 1150, or 1160 in interface 1100, and the method 1400 ends at step 1480.

Figure 15:
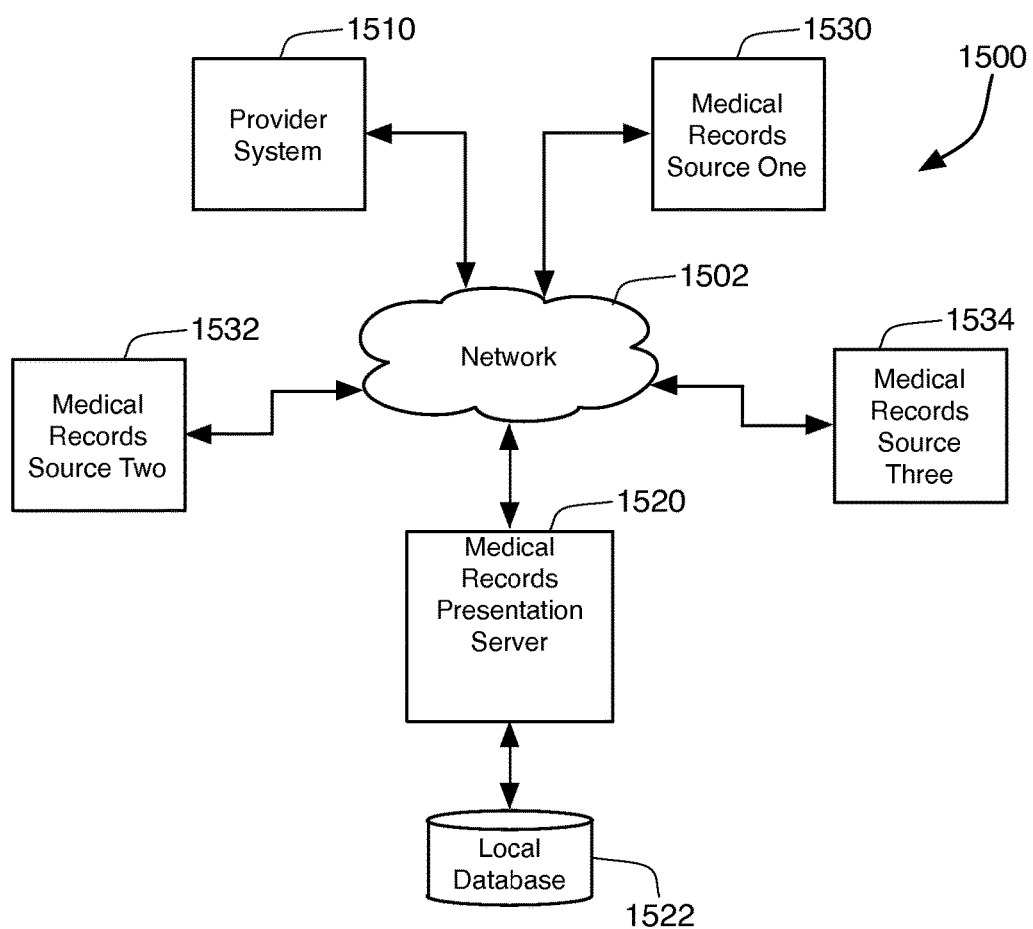
FIG. 15 is a schematic diagram showing an alternative embodiment of the present invention including a presentation server and medical record source servers.

FIG. 15 shows an alternative embodiment system 1500 where a provider system 1510 is used by user-providers to access the medical data of patients. To do this, the provider system 1510 communicates with a medical records presentation server 1520, which in turn implements the methods described above to organize and present medical data. In FIG. 15, medical records are not necessarily stored and managed locally by the presentation server 1520, but instead are stored and managed by one or more medical records source servers 1530, 1532, 1534. Each of the medical records source servers 1530, 1532, 1534 contains medical records from a variety of patients. The different medical records source servers 1530, 1532, 1534 may be managed and controlled by different companies, such as physician practice groups, hospitals, medical holding companies, or medical insurance companies. A single patient may have medical data that is stored on one or all of these medical records source servers 1530, 1532, 1534.

Each of these systems and servers 1510, 1520, 1530, 1532, and 1534 are implemented using one or more physical computer systems having programmed digital processors. In this way, these devices 1510, 1520, 1530, 1532, 1534 are similar to the medical records server 100 described above in connection with FIG. 1.

When a user-provider uses the provider system 1510 to access the medical records presentation server 1520, their computer system 1510 establishes a digital network connection with this server 1520 over a computer network, such as network 1502. The user-provider then requests that the presentation server 1520 provide medical data for a particular patient. While the medical records presentation server 1520 may manage some patient data locally, it is expected that the medical records presentation server 1520 will have to query one or more medical records source servers 1530, 1532, 1534 to obtain all of the medical data that is available concerning the particular patient. This query will also take place over a computer network, which may or may not be the same physical network 1502 that is used by the provider system 1510 to communicate with the medical records presentation server 1520.

In response to these queries, the medical records presentation server 1520 will receive documents, orders, and other medical data relating to the particular patient from one or more of the medical records source servers 1530, 1532, 1534. Note that this data could be organized in a variety of different formats, using medical record data structures that have been developed by competing vendors of medical record software. In order to use this data, it may be necessary for the medical records presentation server 1520 to interpret or translate the data into a common data format. The translation of medical record data from one format to another is well known in the prior art. The medical records presentation server 1520 will then add in any relevant data that it stored locally, and then merge all of this data for presentation to the user-provider that is using the provider system 1510. In presenting this information to the user-provider, the medical records presentation server 1520 will use the methods described above, such as those methods shown in FIGS. 10 and 14, to organize the data before presenting it to the user-provider.

In some embodiments, a particular physician may be associated with a plurality of hospitals or practice groups that store data in different medical records source servers 1530, 1532, 1534. In these embodiments, the medical records presentation server 1520 may be designed to restrict its queries to those medical records source servers 1530, 1532, 1534 that are known to contain data created by the user-provider currently accessing the server 1520. In other embodiments, the presentation server 1520 will query all medical records source servers 1530, 1532, 1534 that may have relevant client data.

In an alternative embodiment, the medical records presentation server 1520 will populate a local, temporary database 1522 based on the records that it receives from the medical records source servers 1530, 1532, 1534. Once the local database 1522 is created, individual queries made by a user-provider from the provider system 1510 would be serviced by the data within the local database 1522 managed by the server 1520. This may allow, for instance, a provider system 1510 to request that the medical records presentation server 1520 pre-populate its local database 1522 overnight with medical data concerning patients that are scheduled to be seen by providers the next day. The medical records presentation server 1520 would be provided with a list of patients to be seen by all providers at a particular clinic, for instance. The server 1520 would query the available medical records source servers 1530, 1532, 1534 for information about all of these patients, and then store this data in its local database 1522. The next day, when a clinic provider requests to view information about a particular patient, the medical records presentation server 1520 could immediately supply this information from its pre-populated database 1522.

As an example, a medical oncology physician may use the provider system 1510 to access records about a particular patient. The medical records presentation server 1520 would acquire medical data about that patient from the medical records source servers 1530, 1532, 1534 and use that to populate a local database 1522. The medical records presentation server 1520 would then use the data in the local database 1522 to organize the data according to the established preferences of the user-provider physician. Such organization may utilize rules to establish document categories of special interest to that user-provider. These rules could distinguish between providers in the user-provider's own medical practice group, and providers that do not work directly with the user-provider but do work in the same medical specialty. The medical records presentation server 1520 would then present the user-provider medical oncology physician the medical data for the particular patient, with the medical data sorted into the following document categories:

1) all notes and other data created by that physician, wherever that data was created and stored throughout the world (assuming accessibility to that data through one of the medical records source servers 1530, 1532, 1534);
2) all notes and other data created by the user-provider's own practice group, namely medical oncology providers working in the same medical practice as the user-provider;
3) all notes and other data created by providers that have been associated with medical oncology in the local database 1522, which may include documents and notes from physicians that have never practiced with the user-provider and in fact may have practices in a different country than the user-provider;
4) all notes and other data created by radiation oncology providers from around the world, including machine-generated data and test results; and
5) all notes and other data created by other providers.

For each of these documents, the system would identify the date associated with the note, the physician, and the location of the physician's practice. Each document would be made available to the user-provider by simply clicking on a link. If possible, all documents presented to the user-provider will have been downloaded to the local database 1522 managed by the medical records presentation server 1520. Where that is not possible, the medical records presentation server 1520 will access any requested document directly from the appropriate medical records source servers 1530, 1532, 1534 whenever a specific document is requested by the user-provider. Furthermore, the summary data 1310, 1320 presented to the user-provider will identify all patient visits for this patient that were found on any of the medical records source servers 1530, 1532, 1534.

In one embodiment, the user-provider would be able to separately view i) notes and other documents, ii) orders, iii) diagnostic studies and lab reports, and iv) prescriptions. In each case, this data would be sorted into categories similar to the five categories listed above.

In yet another embodiment, the system 1500 could be designed to monitor the behavior of the user-provider when using the system 1500. The system 1500 could provide access to external data sources other than the medical records source servers 1530, 1532, 1534, and track the user's use of this data. If trends are identified for a particular user, the system 1500 could respond to those trends. For instance, if a user routinely accesses a particular external data source, the server 1520 could provide simplified access to that external data source every time the user accessed the server 1520.

The many features and advantages of the invention are apparent from the above description. Numerous modifications and variations will readily occur to those skilled in the art. Since such modifications are possible, the invention is not to be limited to the exact construction and operation illustrated and described. Rather, the present invention should be limited only by the following claims.

What is claimed is:

1. A computerized method for providing an improved user interface to data records comprising:
   a) at a server computer, accessing a database comprising:
      i) data records, ii) user records, with each user record being associated with a plurality of data records indicating authorship of the data record, iii) group records associated with a plurality of user records, b) at the server computer, receiving a plurality of rules for organizing data records, each rule being applicable to a subset of user records, the rules establishing requirements to define a subset of the data records;

c) at the server computer, receiving an identification of a desired group of data records from a viewing user desiring to view the data records through a graphical user interface, and then i) associating the viewing user with a viewing user record;

ii) identifying a viewing group record that is associated with the viewing user record, and iii) identifying a group-affiliated set of user records that are associated with the viewing group record;

d) at the server computer, identifying a first subset of the desired group of data records, the first subset being associated with the viewing user record to indicate authorship;

e) at the server computer, identifying a second subset of the desired group of data records comprising data records not in the first subset and associated with at least one of the group-affiliated set of user records to indicate authorship;

f) at the server computer, identifying at least one rule of the plurality of rules applicable to the viewing user record;

g) at the server computer, applying the at least one rule to identify a third subset of the desired group of data records, the third subset comprising data records in the desired group of data records that meet the requirements of the at least one rule and are not in either of the first and second subsets;

h) at the server computer, identifying a fourth subset of the desired group of data records comprising those data records in the desired group of data records that are not in any of the first, second, and third subsets; and i) at the server computer, presenting over the graphical user interface the desired group of data records divided into the following interface subcomponents:

i) a first user-provider document subcomponent containing the first subset of the desired group of data records, ii) a second group providers document subcomponent containing the second subset of the desired group of data records, iii) a third rule-based document subcomponent containing the third subset of the desired group of data records, and iv) a fourth other documents subcomponent containing the fourth subset of the desired group of data records, wherein each interface subcomponent comprises a list of documents available in the applicable subset.

2. The method of claim 1, wherein the at least one rule comprises a first group rule that applies to any user record in the group-affiliated set of user records.

3. The method of claim 2, wherein the at least one rule comprises a second rule that applies only to the viewing user record.

4. The method of claim 2, wherein the plurality of rules comprises other rules that do not apply to the viewing user record.

5. The method of claim 4, wherein the other rules comprise a second group rule that applies to any user record associated with a second group record.

6. The method of claim 1, wherein the at least one rule comprises a first rule that applies only to the viewing user record and to no other user record.

7. The method of claim 1, wherein the database further comprises user type records, wherein each user record is associated with a single user type record, and further wherein the viewing user record is associated with a viewing type record.

8. The method of claim 7, wherein the at least one rule comprises a first rule that applies only to user records associated with both the viewing type record and the viewing group record.

9. The method of claim 1, further comprising the step of providing through the graphical user interface a mechanism to separately show and hide the first, second, third, and fourth subsets.

10. The method of claim 1, wherein the data records are medical data records, the user records identify medical health care providers, and the identification of the desired group of data records is the identification of a patient identifier that is associated with medical data records for a patient.

11. The method of claim 10, further comprising presenting through the user interface summary information derived from services described in the set of medical data records associated with the patient.

12. The method of claim 11, wherein the summary information indicates when the patient was last seen by the medical health care provider identified by the viewing user record, and further indicates when the patient was last seen by any medical health care provider identified by any of the group-affiliated set of user records.

13. The method of claim 10, wherein the medical data records describe data relating to medical orders, diagnostic studies and lab reports, and prescriptions.

14. The method of claim 1, wherein the graphical user interface includes an element that allows the viewing user to select a new point-of-view group that changes the viewing group associated with the viewing user.

* * * * *